United States Patent [19]
Allen et al.

[11] Patent Number: 5,312,354
[45] Date of Patent: May 17, 1994

[54] SAFETY TROCAR INSTRUMENT HAVING A RETRACTABLE POINT ACTUATED BY A TRIGGER SLEEVE

[75] Inventors: William J. Allen, Stratford; Jeffrey A. Stein, Milford, both of Conn.

[73] Assignee: American Cyanamid Company, Stamford, Conn.

[21] Appl. No.: 787,182

[22] Filed: Nov. 4, 1991

[51] Int. Cl.⁵ .............................................. A61M 5/20
[52] U.S. Cl. ........................... 604/157; 128/753; 128/754; 604/164; 604/156; 606/167; 606/172; 606/184; 606/185
[58] Field of Search .................. 606/167-168, 606/172-173, 177, 181-182, 184-185; 604/130, 156-157, 161-162, 164-165, 167; 128/754, 755, 753

[56] References Cited
U.S. PATENT DOCUMENTS

| | | | |
|---|---|---|---|
| 4,207,887 | 6/1980 | Hiltebrandt et al. | 128/207.28 |
| 4,535,773 | 8/1985 | Yoon | 604/51 |
| 4,601,710 | 7/1986 | Moll | 604/165 |
| 4,654,030 | 3/1987 | Moll et al. | 604/165 |
| 4,902,280 | 2/1990 | Lander | 604/165 |
| 4,931,042 | 6/1990 | Holmes et al. | 604/164 |
| 4,943,280 | 7/1990 | Lander | 604/169 |
| 5,013,294 | 5/1991 | Baier | 604/26 |
| 5,030,206 | 7/1991 | Lander | 604/164 |
| 5,066,288 | 11/1991 | Deniega et al. | 604/274 |
| 5,073,169 | 12/1991 | Raiken | 604/180 |
| 5,116,353 | 5/1992 | Green | 606/184 |
| 5,152,754 | 10/1992 | Plyley et al. | 604/164 |

FOREIGN PATENT DOCUMENTS

| | | |
|---|---|---|
| 0424002 | of 0000 | European Pat. Off. . |
| 0461568 | 6/1991 | European Pat. Off. . |
| 0499457 | 2/1992 | European Pat. Off. . |
| 479130 | 4/1992 | European Pat. Off. . |

*Primary Examiner*—Randall L. Green
*Assistant Examiner*—P. Zuttarelli
*Attorney, Agent, or Firm*—Fitzpatrick, Cella, Harper & Scinto

[57] ABSTRACT

A safety trocar instrument, for piercing the wall of an anatomical cavity to provide communication with the inside of the cavity, includes a tubular cannula and an elongate trocar having a sharp piercing point. The trocar is mounted for axial reciprocal movement within the cannula between a withdrawn rest position in which the point is received within and shielded by the distal end of the cannula and a projecting position in which said point is exposed beyond the distal end of the cannula. A retraction spring biases the trocar to its withdrawn position. A latch latches the trocar in the projecting position in opposition to the retraction spring, and a trip member can trip the latch to unlatch the trocar and thereby permit the trocar to be moved to its withdrawn rest position by the retraction spring. A mechanical trigger in the form of a trigger sleeve is mounted within the instrument. Its distal end is locatable between the extreme of said trocar point and the distal end of the cannula to sense counterforce exerted by the cavity wall after it has begun to be pierced by the trocar point and to sense relief of such counterforce when that distal end has cleared the cavity wall. The trigger sleeve is mechanically coupleable to the trip member to cause it to trip the latch in response to sensing relief of such counterforce.

21 Claims, 6 Drawing Sheets

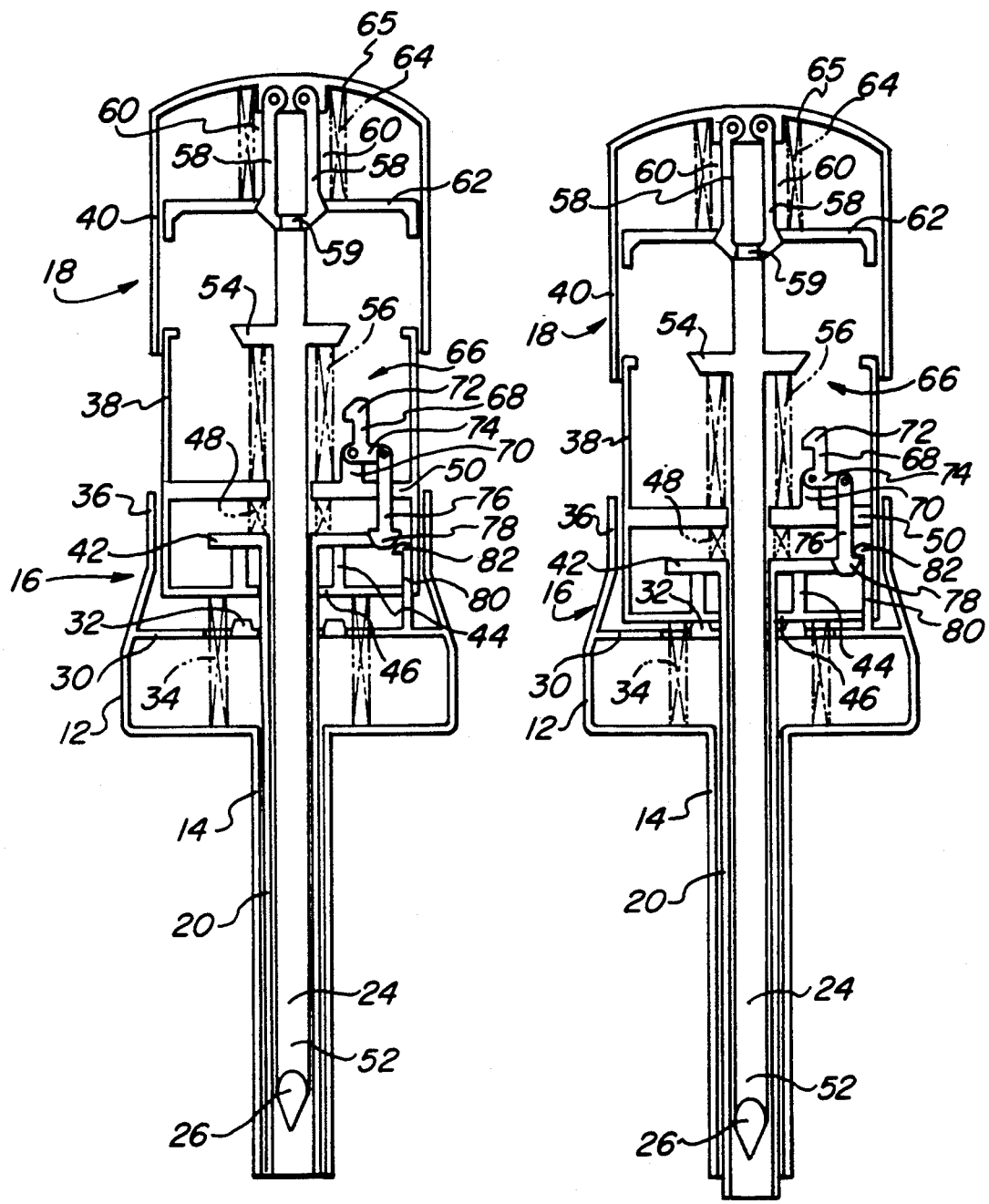
FIG. 3-A    FIG. 3-B

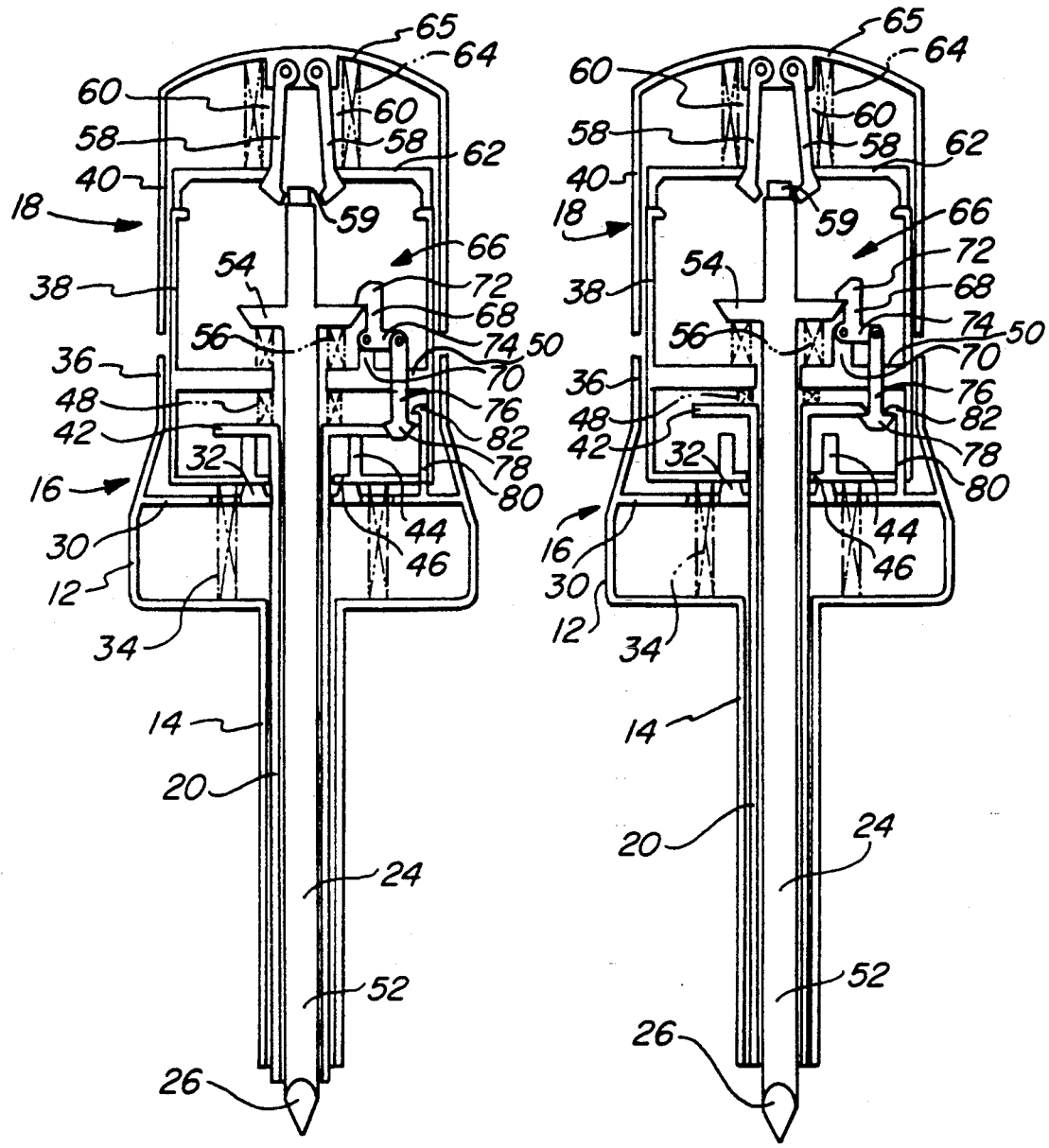
FIG. 3-C   FIG. 3-D

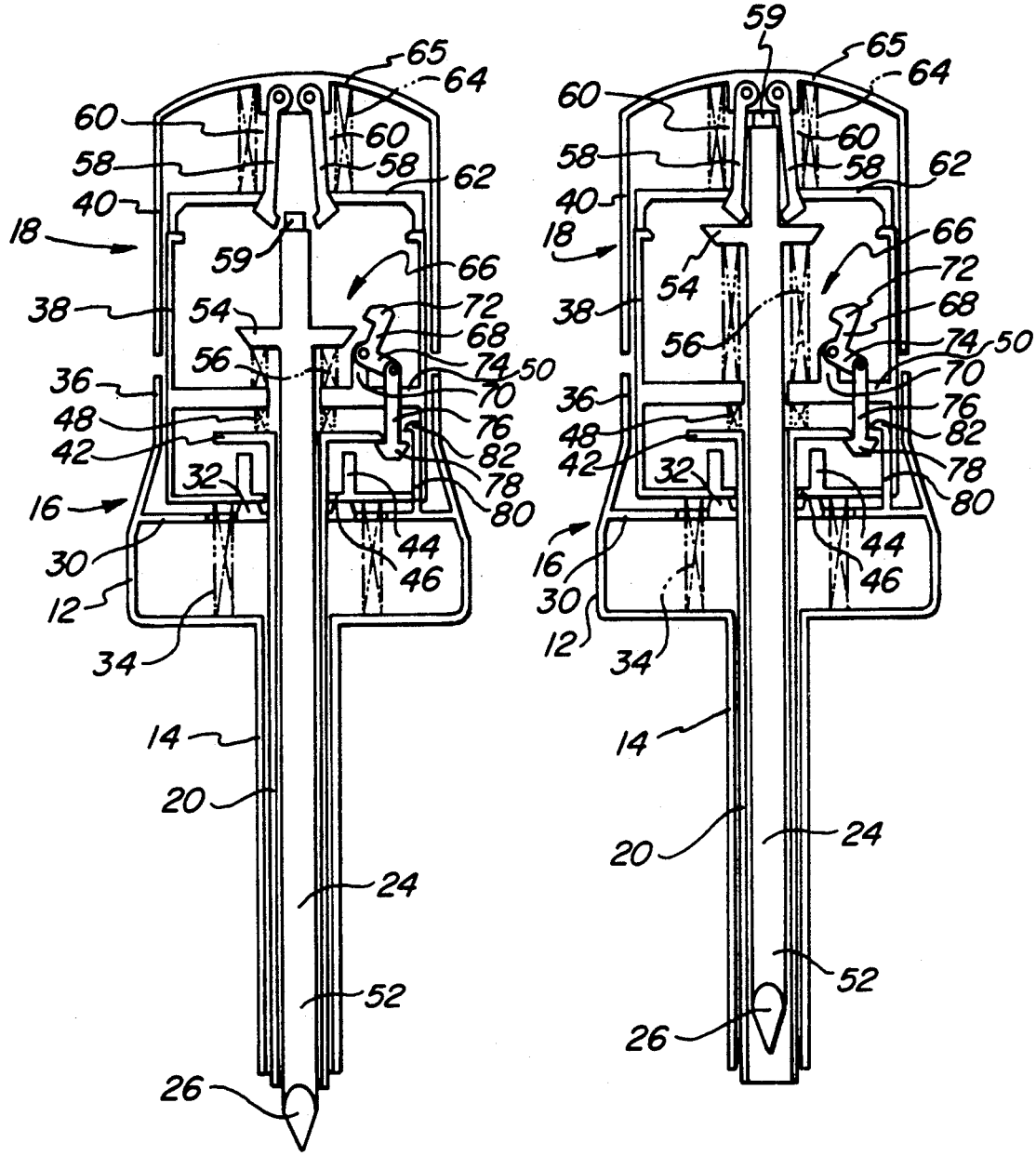

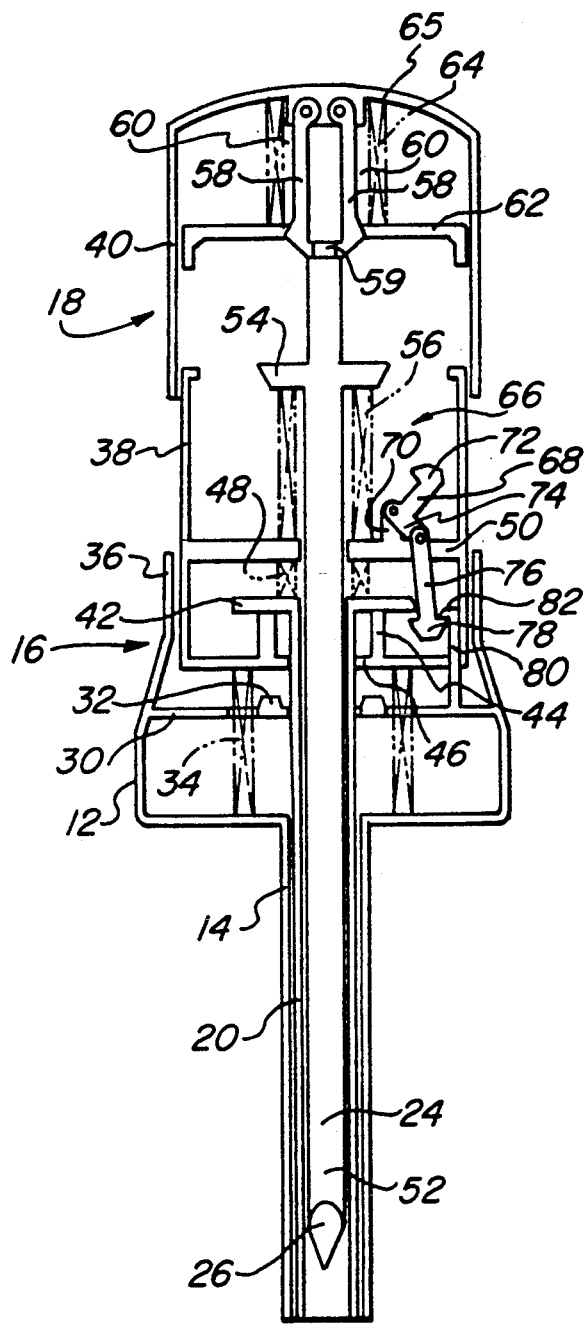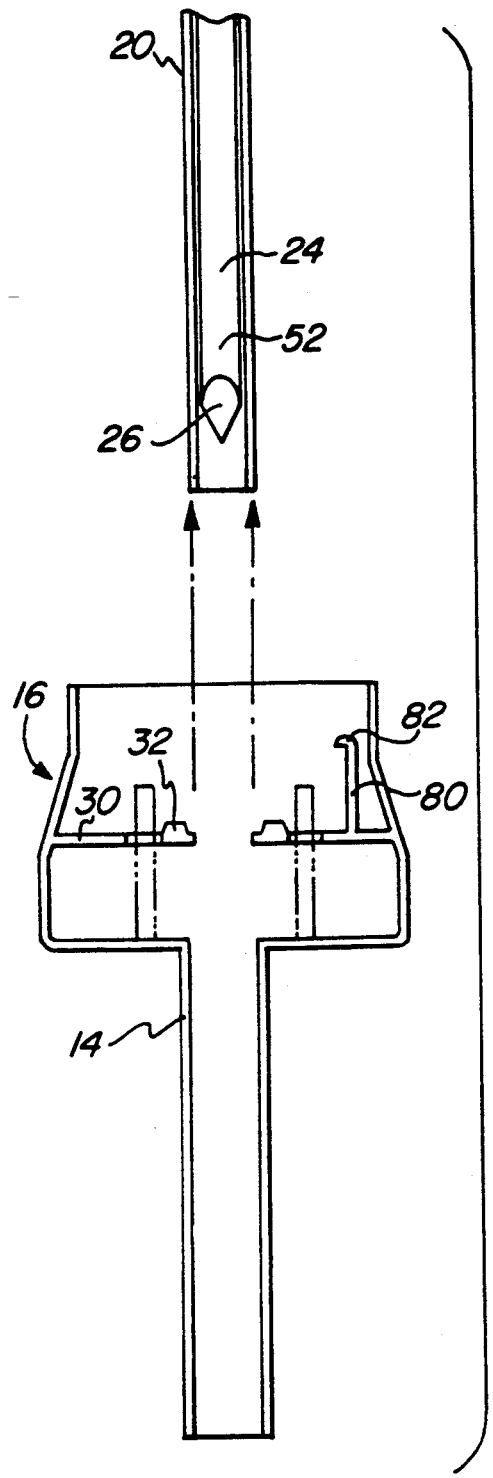
FIG. 4-C          FIG. 4-D

SAFETY TROCAR INSTRUMENT HAVING A RETRACTABLE POINT ACTUATED BY A TRIGGER SLEEVE

BACKGROUND OF THE INVENTION

1. Field of the Invention

The present invention relates to a surgical instrument, commonly called a "trocar instrument" or "device," or simply a "trocar," that is used to pierce the wall of an anatomical cavity thereby forming a passageway providing communication with the inside of the cavity. Other medical instruments such as endoscopes, arthoscopes, and operating instruments can thereafter be inserted through the passageway to perform various medical procedures within the anatomical cavity.

Surgical techniques using trocar devices to pierce anatomical cavity walls have recently gained great favor in the expanding field known as "least invasive surgery." Such techniques have been widely employed, for example, in gall bladder surgery and their use for other types of operations is actively being explored and implemented. These methods are desirable because the passageway formed by the trocar is small and neat. Therefore, the major trauma associated with large surgical incisions, used to perform certain operations in the past, can be avoided.

The present invention provides an improved safety trocar instrument that is well suited to least invasive surgical techniques. By its design the safety trocar instrument of the present invention not only avoids the trauma that results when large incisions are made in an anatomical cavity wall, but also reduces the chance that unintended and unwanted trauma will result particularly after the instrument penetrates the wall.

2. Description of the Prior Art

In its elemental form, a trocar is a device comprising an elongated shaft of, for example, surgical steel having a sharpened blade or point. Typically, least invasive surgery using such a device is performed first by inserting a fine surgical or "Veress" needle through the cavity wall and thereafter injecting a fluid into the cavity to insufflate it and separate the cavity wall, including muscle and the peritoneum in the case of the abdomen, from other internal organs like the heart, stomach, and major blood vessels. The sharpened point of the trocar is then placed against the cavity wall and urged to pierce it by manually applying pressure to the proximal end of the shaft. An outer sleeve or "cannula" may be slid over the shaft through the wound created by the sharp point. The sleeve permits the shaft to be withdrawn from the cavity wall and maintains the passageway into the cavity. Observation and surgical instruments can then be introduced into the cavity through the sleeve.

Ordinarily, the cavity wall exerts relatively large resistance to penetration by the trocar point. However, once the wall is pierced that resistance is relieved, often suddenly, so that the sharp trocar point may suddenly be urged deeply into the cavity. Therefore, the risk exists that the sharp trocar point will injure vital organs in the cavity. Accordingly, attempts have been made to reduce that risk.

For example, U.S. Pat. No. 4,654,030 (Moll, et al.) discloses a safety trocar device that includes a trocar subassembly and a trocar tube subassembly that interfit with, but are separable from, one another. The trocar subassembly includes a grip, a trocar or "obturator" having a sharpened piercing tip or point, an axially reciprocally mounted tubular obturator sleeve or shield, and a compressed coil spring for urging the shield forwardly essentially to surround and shield the piercing tip of the obturator. The trocar tube subassembly includes a main body and an elongated trocar tube. The trocar device is used by inserting the obturator and shield of the trocar subassembly into the trocar tube of the trocar tube subassembly. The shield and piercing tip are together urged to extend through the lumen of the trocar tube. Ordinarily, the shield is locked in this extended position. However, when unlocked the shield may withdraw into the trocar tube against the urging of the compressed spring in the trocar subassembly.

In order to pierce an anatomical cavity wall, the shield is first unlocked. Its exposed distal end is placed against the anatomical cavity wall by applying pressure to the assembly. The resistance exerted by the wall causes the shield to retract axially into the trocar tube thereby to expose the piercing tip of the obturator. Thus the tip may puncture the cavity wall. Once the tip and shield have penetrated the wall and have entered the anatomical cavity, the resistance exerted by the wall on the distal end of the shield is relieved permitting it to be urged by the compressed spring back to its extended position surrounding the piercing tip. Accordingly, once the resistance of tee cavity wall on the distal end of the shield is released, the chances of injury to internal organ structures are reduced because the sharp portions of the piercing tip are again covered by the shield.

U.S. Pat. No. 4,535,773 (Yoon) also relates to a safety puncturing instrument or trocar for puncturing an anatomical cavity wall and discloses several embodiments of that instrument. A number of the embodiments are conceptually similar to that disclosed in the Moll Patent and include an outer sleeve or obturator tube and elongated section defining an interior lumen opening at a distal end and extending through to a proximal end. A thin-walled inner sleeve or shield is mounted coaxially within the outer sleeve and is urged by a compression spring to protrude from the lumen at the distal end of the outer sleeve. A trocar or obturator has a sharp blade at its distal end that can be inserted into the inner sleeve so that, when seated, the blade projects beyond the distal end of the outer sleeve but is encircled and shielded by the distal end of the inner sleeve.

These embodiments of the safety puncturing instrument disclosed in the Yoon Patent are used by inserting the trocar into the inner and outer sleeves and placing the distal end of the inner sleeve against the wall of an anatomical cavity. Force is then applied to the proximal end of the trocar so that the outer sleeve and trocar blade are forced toward the cavity wall. The distal end of the inner sleeve is urged to retract within the distal end of the outer sleeve by resistance exerted by the cavity wall, thereby compressing the spring and permitting the trocar blade to be exposed to pierce the wall.

When the outer sleeve enters the wound created by the trocar blade, the inner sleeve is held completely within the outer sleeve by the resistance of the cavity wall to passage of the distal ends of the outer and inner sleeves. As force continues to be applied to the proximal end of the trocar, the sharp point passes through the cavity wall and enters into the cavity. The force also causes the outer sleeve to follow through the wound. As the distal ends of the outer and inner sleeves clear the inner surface of the inside of the cavity wall, the resistance of the wall is relieved thereby releasing the inner sleeve, which is then returned to its extended position by the spring to shield the trocar blade.

Safety trocars like those described above and disclosed in the Moll and Yoon Patents have certain inherent drawbacks. First, because the piercing tip of the trocar blade is generally shielded when the instrument is placed against the anatomical cavity wall, it is necessarily shielded from the surgeon's view. Therefore, he or she cannot be certain that the tip will puncture the wall at the precise location desired. Moreover, after the piercing tip has penetrated the cavity wall, it must protrude a further substantial distance into the anatomical cavity before the inner sleeve or shield is released again to cover the tip. Thus, a substantial period remains during which the tip is exposed and may injure internal organ structures. In the Yoon devices, since the inner sleeve or shield and outer sleeve may remain in the cavity after the trocar is removed, they often project a substantial distance into the cavity. Thus the available space in the cavity within which the surgeon can work is reduced.

The Yoon Patent also discloses another embodiment, shown in its FIGS. 34 and 35, that includes structure for causing the sharp trocar point to retract inwardly into the outer sleeve. More particularly, this structure includes a puncturing implement or trocar having a shaft with a large diameter section at its distal end terminating in a sharp blade and a point that bears one or more electrical pressure sensors or transducer elements. An intermediate section of the trocar has a reduced diameter and is able to slide within a hollow proximal tubular section. A tension spring is coupled between the proximal end of the intermediate shaft section and a plug threaded into the proximal end of the tubular section. A detent mechanism holding a small detent is mounted in the intermediate shaft section. The detent is urged radially outwardly by a compression spring. When the intermediate shaft section is fully extended outwardly from the tubular section, the detent is coaxially aligned with and protrudes radially into a small hole in the wall of that tubular section. Thus, the shaft of the trocar is locked in the fully extended position against the urging of the coil spring, which is then held in tension.

The whole assembly is carried in an outer sleeve. When the trocar is locked in the extended position, its blade extends beyond the distal end of that sleeve.

Electrical leads pass through the interior of the shaft of the trocar and connect the blade sensors to electrical contacts within the detent, and in turn to an electrical socket.

To use the instrument, the trocar is first locked in its outwardly extended position with the detent radially engaged in the detent hole. The trocar-tubular section assembly is then fitted with a handle and the distal end of the trocar is inserted into the outer sleeve. When that assembly is fully inserted into that sleeve, the detent is coaxially aligned with a radial solenoid socket adjacent the electrical socket. An electrical plug assembly includes an electrical jack that connects the leads from the blade sensors through the socket to an alarm network.

The trocar assembly may then be used by pressing the blade against the anatomical cavity wall such that counterforce exerted by that wall on the blade sensors is converted to a sequential set of ready signals that trigger the alarm network. As the blade passes through the wall into the cavity interior, the counterforce is relieved from the blade sensors sequentially to produce a set of electrical signals through the alarm network. When the penetration is complete, the electrical signals from the sensors cause the alarm network to actuate the solenoid, thereby depressing the detent to permit the tension spring to retract the blade into the sleeve.

An alternative detent structure is illustrated in FIG. 36 of the Yoon Patent.

While in many respects this latter embodiment of the Yoon invention is an improvement over the other safety trocar designs described in the Yoon and Moll Patents, it nevertheless suffers from certain serious disadvantages. First, it depends on electrical pressure sensors or transducer elements connected to an alarm network to sense release of the counterforce exerted by the anatomical cavity wall and thereby to trigger retraction of the trocar point. Therefore, proper operation of the device may be destroyed by an electrical power failure or interruption that, even if brief, can result in serious injury to the patient. Further, the device is not self-contained but must instead be connected to the external alarm network. That alarm network may be cumbersome and the electrical leads connecting the trocar device to the alarm network may well interfere with the surgeon's work.

Therefore, still additional improvement to safety trocar instrument design would be greatly beneficial to the surgical community.

SUMMARY OF THE INVENTION

It is a principal object of the present invention to provide an improved safety trocar instrument that mitigates the problems associated with prior devices of the type disclosed in the Moll and Yoon Patents and having a safety shield that projects forwardly to surround a sharp trocar point after the point and distal end of the shield penetrate an anatomical cavity wall.

It is an additional principal object of the present invention to provide a self-contained, mechanically actuated safety trocar instrument in which a sharp trocar point is retracted into a surrounding sleeve when the sharp point has penetrated an anatomical cavity wall. The invention thereby results in a substantial improvement over known devices such as the latter embodiment described in the Yoon Patent.

These and other objects are achieved by the present invention, which in a preferred embodiment includes a main body that supports an outer sleeve or cannula.

The main body is configured to mate with a trigger sleeve and trocar subassembly that includes a main housing and a plunger head in which a trigger sleeve is axially reciprocally mounted. The trigger sleeve is urged to a rest position projecting outwardly from the main housing. A trocar having a sharp point is coaxially received within the trigger sleeve for reciprocal movement and is urged to a retracted rest position with the sharp point surrounded by the distal end of the sleeve.

The safety trocar instrument in accordance with this preferred embodiment is assembled by mating the main body-cannula subassembly with the trigger sleeve-trocar subassembly with the inner sleeve and trocar received coaxially within the cannula.

This instrument is armed to pierce an anatomical cavity wall by manually pressing the plunger head of the trigger sleeve-trocar subassembly into the main body until the distal end of the trigger sleeve projects slightly beyond the distal end of the cannula and thereafter the sharp trocar point projects beyond the distal end of the trigger sleeve. The trocar is latched in such attitude by an internal latching mechanism residing in the plunger head and main housing of the trigger sleeve-trocar subassembly, but the trigger sleeve remains free to reciprocate by being urged back into the cannula. The trocar instrument is then used to pierce an anatomical cavity wall by pressing the exposed point of the trocar against the wall at precisely the desired location. After the point begins to penetrate the wall, the distal end of the trigger sleeve encounters the outer surface of the wall. The resistance of the wall thereafter causes the trigger sleeve to be urged inwardly into the cannula to a retracted position in a first stage preparatory to disarming the latching mechanism. When the cavity wall has been completely penetrated pressure on the trigger sleeve is relieved permitting it again to be urged back to its rest position. The return of the trigger sleeve then fully disarms the latch mechanism thereby releasing the trocar shaft and permitting it to be retracted to its rest position with its sharp point surrounded by the trigger sleeve and cannula. The trocar shaft and trigger subassembly can then be removed leaving the cannula in the anatomical cavity wall to provide communication with the inside of the cavity.

Thus the present invention provides a safety trocar instrument in which the sharp point of the trocar is retracted into a surrounding shield structure. Since retraction occurs immediately upon entry of the distal end of the trigger sleeve into the anatomical cavity, there is a reduced likelihood of injury to internal organs. Moreover, since retraction occurs upon entry of the distal end of the trigger sleeve into the cavity, little of the device remains in the cavity after penetration to infringe upon the surgeon's work area. Still further, the trocar point is exposed to the surgeon's view at the start of penetration so that he or she can precisely position it at the desired cavity wall location. Thus the safety trocar instrument of the present invention is a substantial improvement over designs of the type disclosed in the Moll Patents and as the initial embodiments in the Yoon Patent.

The present invention is also entirely self-contained and mechanically actuated. Therefore, it is not affected by electrical power failures or interruptions nor does it depend on cumbersome ancillary electrical equipment. And since no wire connections to such ancillary equipment are required, they are not present to interfere with the surgeon's work.

These and other objects, aspects, features, and advantages of the present invention will become apparent from the following detailed description taken in conjunction with the accompanying drawings.

BRIEF DESCRIPTION OF THE DRAWINGS

FIGS. 3A to 3D are a sequence of vertical cross-sectional views of the safety trocar instrument of the present invention showing it being armed and operated through initial piercing of an anatomical cavity wall; and FIGS. 4A to 4D are a sequence of vertical cross-sectional views of the safety trocar instrument of the present invention showing the trocar retraction operation and the trigger sleeve-trocar subassembly being removed from the main body-cannula assembly.

DETAILED DESCRIPTION OF THE PREFERRED EMBODIMENT

Figure 1:
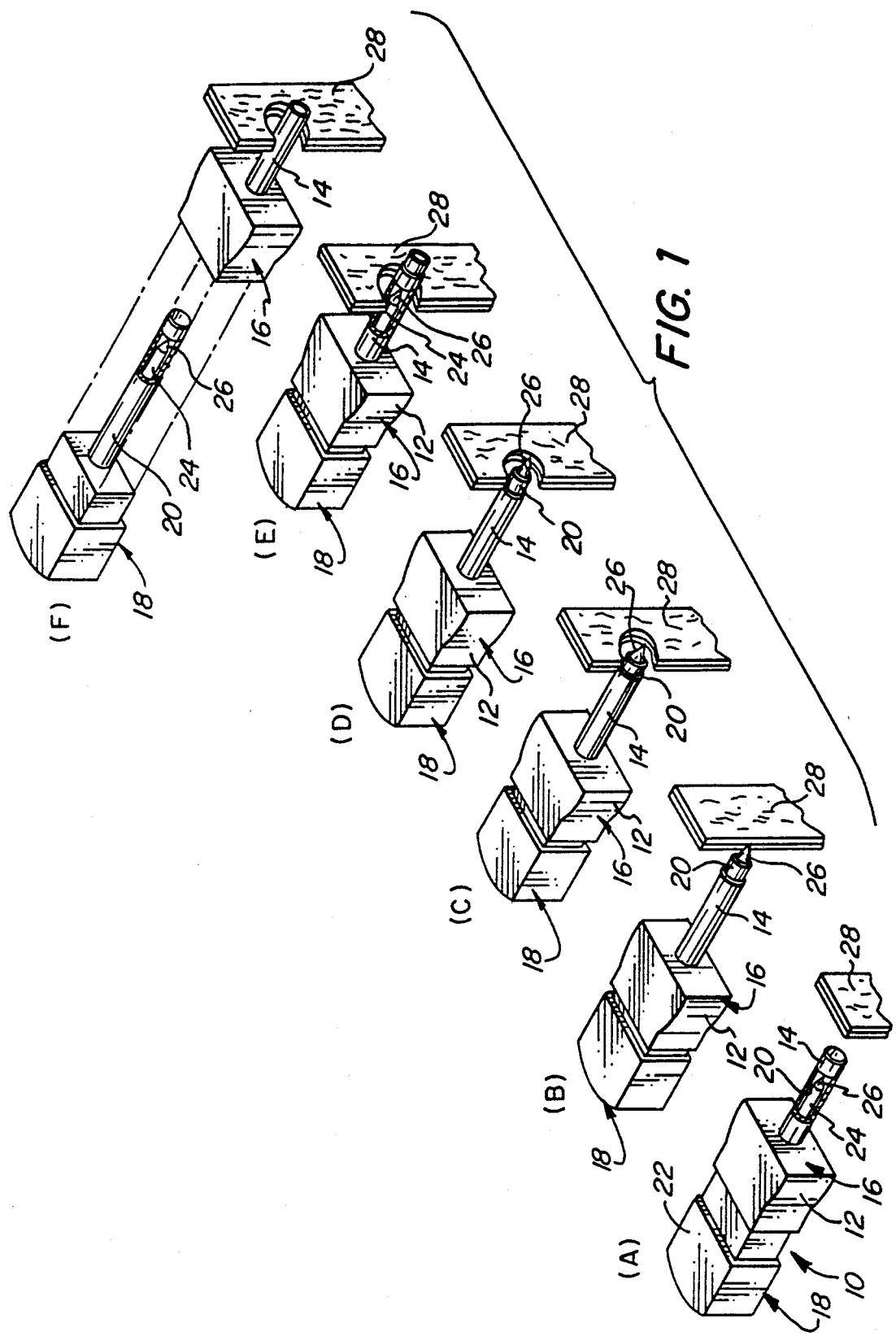
FIGS. 1A to 1F are a sequence of perspective views of the preferred embodiment of the safety trocar instrument of the present invention showing it at various stages during use.

FIGS. 1A though 1F diagrammatically show the safety trocar instrument in accordance with the preferred embodiment of the present invention as it appears in various stages of use. More particularly, this safety trocar instrument, generally indicated at 10, includes a main body 12 having an outer tubular sleeve or cannula 14 projecting from it. The main body-cannula subassembly, generally indicated at 16, is configured to mate with a trigger sleeve-trocar subassembly generally indicated at 18, that includes a tubular trigger sleeve 20, mounted for reciprocal movement in a housing 22 and urged to an outwardly extending position therefrom, and an elongate trocar 24, having a sharp point 26 and being mounted for axial reciprocal movement in the trigger sleeve 20 but being urged to a retracted position therein.

In the assembled rest position of the instrument 10 shown in FIG. 1A, in which the trigger sleeve 20 and cannula 14 are partly broken away to show the location of the trocar point 26, the trigger sleeve-trocar subassembly 18 is mated with the main body-cannula subassembly 16 such that the coaxially arranged trocar 24 and trigger sleeve 20 are in turn received coaxially within the cannula 14. As can be seen, in this rest position the distal end of the trigger sleeve resides substantially entirely within the distal end of the cannula and the sharp point 26 of the trocar resides within the distal end of the trigger sleeve 20. Thus, in the rest position the trigger sleeve and cannula shield the trocar point 26.

The assembled instrument is armed, as shown in FIG. 1B, to pierce an anatomical wall, diagrammatically illustrated at 28, by manually squeezing the trigger sleeve-trocar subassembly 18 into the main body-cannula subassembly 16. This operation causes the distal end of the trigger sleeve 20 to project beyond the distal end of the cannula 14 and causes the sharp trocar point 26 to project beyond the distal end of the trigger sleeve 20. The trocar is latched in this projecting position by an internal latching mechanism to be described in detail below. Thus the trocar point is exposed in preparation for puncturing the cavity wall 28.

As shown in FIGS. 1B and 1C, the trocar point 26 is visible to a surgeon so that it can be precisely positioned at the desired location on an anatomical cavity wall 28 for the intended puncture wound. As the point begins penetration, counterforce exerted by the wall 28 urges the distal end of the trigger sleeve 20 back into the distal end of the cannula to a first position. In this first retracted position, the trigger sleeve is prepared to disarm the internal latch mechanism holding the trocar in its extended position.

FIG. 1D shows the state of the trocar instrument 10 in which both the trocar point and the distal ends of the trigger sleeve and cannula have cleared the inside surface of the wall 28. Accordingly, the counterforce exerted by the wall on the trigger sleeve is relieved permitting it again to be projected to its extended position with its distal end protruding beyond the distal end of the cannula. This action of the trigger sleeve disarms the internal latch mechanism permitting the trocar to be retracted to its rest position with the trocar point within the trigger sleeve distal end, as shown in FIG. 1E. In FIG. 1E the trigger sleeve and cannula are shown partly broken away for clarity as in FIG. 1A.

Finally, as shown in FIG. 1F, the trigger sleeve-trocar subassembly 18 can be withdrawn from the main body-cannula subassembly 16 with the cannula 14 remaining in the puncture wound in the wall 28. The cannula thus provides a passage through the cavity wall into the cavity interior.

The specific structure of the safety trocar instrument 10 in accordance with a preferred embodiment of the present invention will now be described with reference to FIG. 2, which is a vertical cross-sectional view thereof. The trocar device includes the main body 12 having the cannula 14 extending therefrom. The main body 12 is formed with an intermediate partition 30, an upwardly projecting stop 32 on the partition 30, and a captured compression spring 34. The main body 12 is also formed with a generally rectangularly shaped socket 36 projecting upwardly from the partition 30.

The trigger sleeve-trocar subassembly 18 is configured to mate with main body-cannula subassembly 16 and has a main housing 38, a plunger head 40, and the trigger sleeve 20, which is reciprocally mounted within housing 38. The bottom of the main housing 38 is rectangularly shaped to be telescopically received in the socket 36. The plunger head 40 is mounted for reciprocal telescoping movement relative to the housing 38 and the two elements are prevented from disengaging from one another by suitable means (not shown).

The trigger sleeve 20 has a rest position relative to the main housing 38 in which a radial flange 42 at its proximal end is supported by a retainer 44 on the bottom 46 of the housing 38. The trigger sleeve is urged to this rest position by a motion spring 48 compressed between the radial trigger sleeve flange 42 and the underside of an inner horizontal partition 50 formed within housing 38.

The trocar 24 is also mounted for axial reciprocal movement within the trigger sleeve-trocar subassembly and includes a shaft 52 having catch means in the form of a radial flange 54 near its proximal end and the sharp point 26 at its distal end. The trocar shaft 52 is coaxially received within the trigger sleeve 20. The trocar 24 is urged to a retracted rest position by a retractor spring 56 compressed between the upper side of the horizontal partition 50 and the radial flange 54. The trocar 24 is also stopped in this retracted rest position by a pair of pivotable pushers 58 mounted in the plunger head 40 that, when closed in the radial direction, engage the proximal end 59 of the trocar shaft 52, which has a reduced diameter. The pivotable pushers 58 each have a downwardly, radially outwardly tapered outer cam surface 60 that is engaged by an inner aperture in an embracing ring 62 mounted in the plunger head 40. The ring 62 is urged downwardly by a plunger spring 64 that is compressed between it and the inner surface of the top 65 of the plunger head 40. The embracing ring 62, which thus constitutes a cam driver, urges the pivotable pushers 58 radially together by engaging the tapered outer pusher surfaces.

In addition, the trigger sleeve-trocar subassembly incorporates a latch mechanism, indicated generally at 66, the function of which was generally described above. Now, in detail, this latch mechanism 66 includes latch means in the form of a pawl 68 mounted for pivoted movement on a stand 70 projecting upwardly from the inner partition 50 within the housing 38. The pawl 68 is formed with a hook 72 that can engage the top of the flange 54 on the trocar shaft 52. A sidewardly projecting arm 74 is formed on the pawl 68 and carries pivotably mounted trip means in the form of a leg 76 that projects downwardly through the partition 50 and has an enlarged foot 78 at its lower free end. This foot is configured to engage the head 82 of an upstanding tab 80 projecting from the partition 30 in the main body through a hole in the bottom 46 of the housing 38. It is this latch mechanism, in cooperation with the trocar flange 54 and the trigger sleeve flange 42, that determines the sequence of operations of the trocar instrument described above with reference to FIGS. 1A to 1F.

More particularly, FIGS. 3A through 3D show the sequence of movements of the various elements of the safety trocar instrument described above from the rest position to arming of the instrument, and, in turn, to initial penetration of the anatomical cavity wall.

Figure 2:
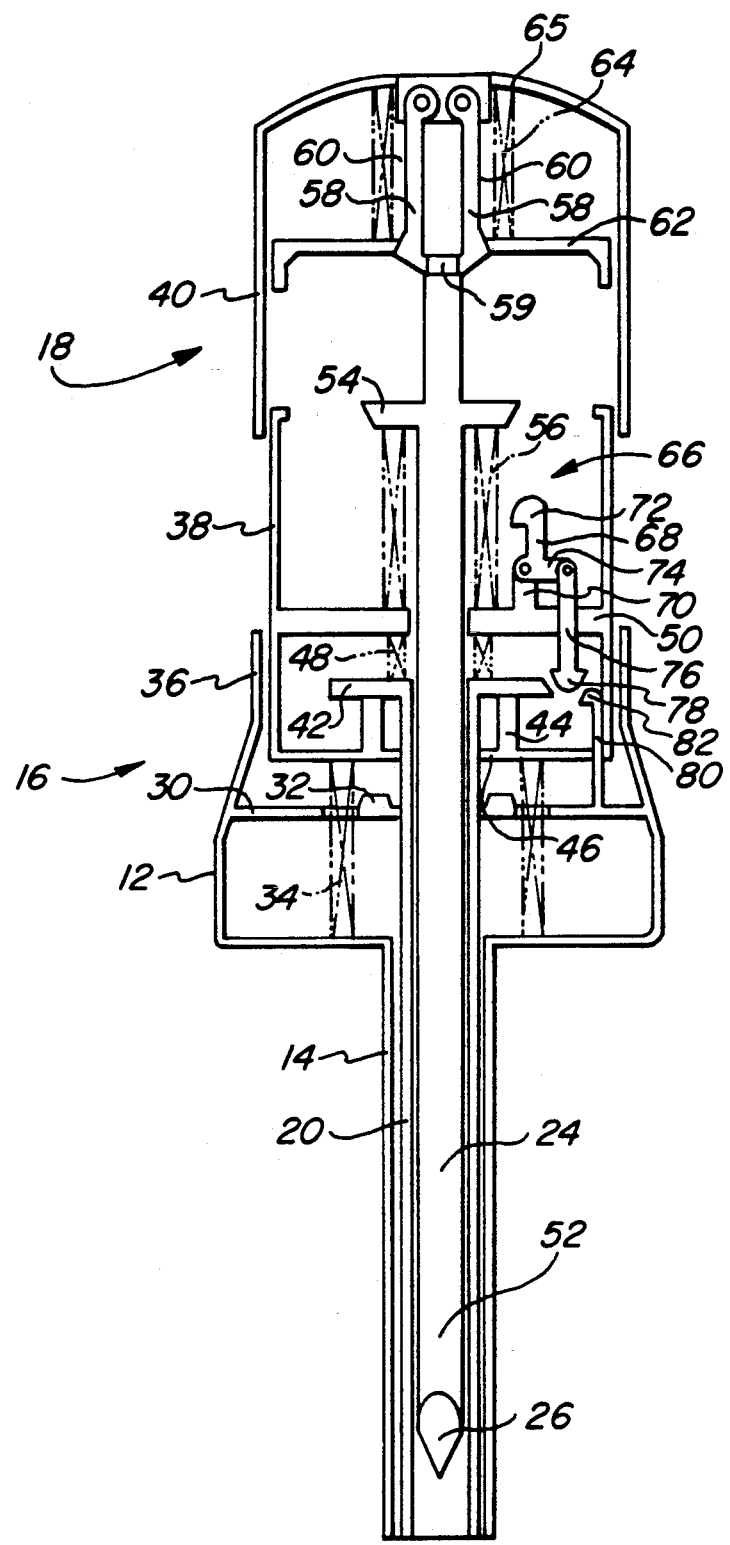
FIG. 2 is a vertical cross-sectional view of the safety trocar instrument of the present invention shown in its assembled rest condition.

In the initial rest position shown in FIG. 3A, which is substantially the same as FIG. 2, the trigger sleeve-trocar assembly 18 is inserted into the main body-cannula subassembly 16 with the trigger sleeve 20 and trocar shaft 52 coaxially received within the cannula 14. The distal ends of trigger sleeve 20 and cannula 14 terminate at about the same axial location, with the main housing 38 being urged outwardly from the main body 12 to its rest position by the relaxed compression spring 34.

When the device is to be used, the trigger sleeve-trocar subassembly 18 is manually squeezed into main body-cannula subassembly 16 thereby compressing the captured spring 34, until the bottom wall 46 of housing 38 abuts the stop 32. In this position, shown in FIG. 3B, the foot 78 of the leg 76 is caught under the head 82 of the tab 80. The distal end of the trigger sleeve 20 projects slightly beyond on the distal end of the cannula 14, but the point 26 of the trocar 24 remains within both trigger sleeve 20 and cannula 14.

Further depression of plunger head 40 relative to the main housing 38 causes the pivotable pushers 58 to push the trocar shaft 54 axially downwardly until the hook 72 of the pawl 68 overrides the flange 54 on the shaft 52. The point 26 of the trocar 24 then projects beyond the distal ends of both the trigger sleeve 20 and cannula 14, as shown in FIG. 3C.

Ultimately, complete depression of plunger head 40 causes the periphery 83 of the embracing ring 62 to engage the upper extreme 84 of the housing 38 thereby stopping relative embracing ring-main housing movement. Further downward movement of the plunger head 40 causes the embracing ring 62 to move upwardly relative to the pushers 58 which are then permitted to spread radially outwardly and release the proximal end 59 of the trocar shaft 52. In this configuration, shown in FIG. 3C, the trocar instrument is armed and ready to pierce an anatomical cavity wall.

The instrument can then create a puncture wound by pressing the point 26 of the trocar 24 against the cavity wall. After the point begins its entry, the distal end of the trigger sleeve encounters the cavity wall. Resistance or counterforce exerted by the wall causes the trigger sleeve 20 to be urged inwardly into cannula 14, against the force of the motion spring 48, until the edge of the radial trigger sleeve flange 42 overrides the foot 78 of the leg 76, as shown in FIG. 3D.

FIGS. 4A to 4D show the sequence of movement of the various elements of the safety trocar instrument as the cavity wall is penetrated and retraction of the trocar point is subsequently triggered. As depicted in FIG. 4A, counterforce against the distal end of the trigger sleeve 20 is relieved when the trigger sleeve and cannula 14 clear the inner surface of the cavity wall so that the motion spring 48 may urge the trigger sleeve 20 downwardly again toward its rest position.

This motion of the sleeve causes the radial flange 42 to pull the leg 76 downwardly thereby pivoting the pawl 68 so that it hook 72 is disengaged from the radial flange 54 on the trocar shaft.

The trocar shaft 52 is thereby released so that its point 26 is once again retracted into the trigger sleeve 20 and cannula 14 by the force of the retractor spring 56, as depicted in FIG. 4B.

When plunger head 40 is thereafter manually released, it may move upwardly within the main housing 38, under the influence of plunger spring 64, permitting the periphery 83 of the embracing ring 62 to clear the upper extreme of the housing 38 and again embrace the outer tapered sides 60 of pivotable pushers 58 to urge the pushers 58 together. The pushers may then again grip the proximal end 59 of the trocar shaft 52, as shown in FIG. 4C. As can also be seen there, the leg 76 can swing about its pivot on the arm 74 so that the foot 78 can be disengaged from both the trigger-sleeve flange 42 and the head 82 of the tab 80. Appropriate biasing means for the latch can be provided to ensure disengagement.

Thereafter the trigger sleeve-trocar subassembly may be removed from main body-cannula subassembly such that the cannula remains in the anatomical cavity wall to provide communication with the cavity interior.

Accordingly, it will be appreciated that the present invention provides an improved safety trocar instrument that retracts a sharpened trocar point into a shielding trigger sleeve as soon as the distal end of the sleeve penetrates an anatomical cavity wall. The instrument may be self-contained and is mechanically actuated. Therefore, reliable operation does not depend on external power supplies or electrical triggering mechanisms.

Although a specific embodiment of the present invention has been described above in detail, it will be understood that this description is merely for purposes of illustration. Various modifications of an equivalent structures corresponding to the disclosed aspects of the preferred embodiment in addition to those described above may be made by those skilled in the art without departing from the spirit of the present invention which is defined in the following claims, the scope of which is to be accorded the broadest interpretation so as to encompass such modifications and equivalent structures.

What is claimed is:

1. A safety trocar instrument for piercing a wall of an anatomical cavity, having an interior, to provide communication with the interior of the cavity, said trocar instrument comprising:
    (a) a tubular cannula having a distal end;
    (b) an elaborate trocar, having a sharp piercing point terminating in an extreme end, mountable for axial reciprocal movement within said cannula between a withdrawn rest position in which said point is received within and shielded by the distal end of said cannula and a projecting position in which said point is exposed beyond the distal end of said cannula;
    (c) means for biasing said trocar to its withdrawn rest position;
    (d) latch means for latching said trocar in the projecting position in opposition to said biasing means;
    (e) trip means for tripping said latching means to unlatch said trocar and thereby permitting said trocar to be moved to its withdrawn rest position by said biasing means;
    (f) mechanical trigger means mounted within said instrument, having a counterforce sensing portion locatable between the extreme end of said trocar point and the distal end of said cannula, said sensing portion sensing a counterforce exerted by the wall of the cavity after it has begun to be pierced by said trocar point and sensing relief of such counterforce when said sensing portion has pierced the wall of the cavity, said trigger means being mechanically coupleable to said trip means to cause said trip means to trip said latch means in response to sensing relief of such counterforce; and
    (g) plunger means for manually moving said trocar from the withdrawn rest position to the projecting position.

2. The safety trocar instrument according to claim 1, wherein said trigger means comprises a tubular trigger sleeve, having a distal end, in which said trocar is coaxially received, and said sensing portion comprises the distal end of said trigger sleeve, said trigger sleeve being mountable coaxially within said cannula for reciprocal movement between an extended rest position with the trigger sleeve distal end located between the extreme end of said trocar point and the distal end of said cannula and a retracted position with the trigger sleeve distal end retracted toward the distal end of said cannula.

3. The safety trocar instrument according to claim 2, wherein said trigger sleeve is mounted to be coupled to said trip means when it is moved to the retracted position and thereafter causes said trip means to trip said latch means when it is returned to its extended rest position.

4. The safety trocar instrument according to claim 3, further comprising means for urging said trigger sleeve to its extended rest position.

5. The safety trocar instrument according to claim 1, further comprising a housing in which said trocar is mounted for said reciprocal movement, wherein said latch means comprises a pawl mounted with said housing, and wherein said trocar includes catch means engageable with said pawl when said trocar is moved to its projecting position.

6. The safety trocar instrument according to claim 5, wherein said trip means includes a trip member coupled to said pawl and coupleable to said trigger means to disengage said pawl from said catch means when said sensing portion senses relief of such counterforce.

7. The safety trocar instrument according to claim 1, further comprising a housing, and wherein:
    said trigger means comprises a tubular trigger sleeve, having a distal end, in which said trocar is coaxially received, and said sensing means comprises the distal end of said trigger sleeve, said trigger sleeve being receivable coaxially within said cannula and being mounted with said housing for axial reciprocal movement between an extended rest position with its distal end located between the extreme end of said trocar point and the distal end of said cannula and a retracted position with its distal end retracted toward the distal end of said cannula;
    said latch means comprises a pawl mounted within said housing;
    said trocar comprises catch means engageable with said pawl when said trocar is moved to its projecting position; and said trip means comprises a trip member linked to said pawl and coupleable to said trigger sleeve when it is moved to its retracted position;

said trigger sleeve moving said trip member when it returns to its extended rest position to disengage said pawl from said catch means permitting said trocar to move to its withdrawn rest position.

8. The safety trocar instrument according to claim 7, further comprising means for urging said trigger sleeve to the extended rest position.

9. The safety trocar instrument according to claim 1, wherein said plunger means comprises means for gripping a portion of said trocar remote from said piercing point when said trocar is in the withdrawn rest position and for releasing said remote portion when said trocar reaches said projecting position.

10. The safety trocar instrument according to claim 9, wherein said plunger means further comprises a plunger head mounted for reciprocal movement relative to said trocar, and wherein said gripping means comprises at least one pusher element mounted in said plunger head, and means for driving said pusher element to grip said trocar in a radial direction and to release said trocar.

11. The safety trocar instrument according to claim 10, further comprising a housing with which said trocar and said plunger head are mounted for reciprocal movement in an axial direction;

wherein said pusher element has an outer cam surface and is mounted within said plunger head for pivoted movement into and out of gripping engagement with said trocar; and wherein said driving means comprises a cam driver mounted in said plunger head cooperating with said cam surface in a first position to hold said pusher element in gripping engagement with said trocar and in a second position to release said pusher element from gripping engagement with said trocar.

12. The safety trocar instrument according to claim 1, wherein said trocar, said biasing means, said trip means, and said trigger means constitute a trigger-trocar subassembly that is removable as a unit from said cannula.

13. A safety trocar instrument for piercing a wall of an anatomical cavity, having an interior, to provide communication with the interior of the cavity, said trocar instrument comprising:

(a) a tubular cannula having a distal end;
(b) a tubular trigger sleeve, having a distal end, mountable for axial reciprocal movement within said cannula between an extended rest position in which its distal end projects beyond the distal end of said cannula and a retracted position in which its distal end is retracted toward the distal end of said cannula from the rest position;
(c) means for urging said trigger sleeve towards its rest position;
(d) an elaborate trocar, having a sharp piercing point, mounted for axial reciprocal movement within said trigger sleeve between a withdrawn rest position in which said point is received within and shielded by the distal end of said trigger sleeve and a projecting position in which said point is exposed beyond the distal end of said trigger sleeve;
(e) means for biasing said trocar to the withdrawn rest position;
(f) latch means for latching said trocar in its projecting position in opposition to said biasing means, in an armed stage of said instrument, in which said trigger sleeve can reciprocate between its extend rest position and its retracted position;
(g) trip means coupled to said latch means, and engaged by said trigger sleeve when said trigger sleeve is moved to its retracted position, for unlatching said latch means from said trocar when said trigger sleeve subsequently returns to its extended rest position, thereby permitting said trocar to be moved to its withdrawn rest position by said biasing means; and
(h) plunger means for manually moving said trocar from the withdrawn rest position to the projecting position.

14. The safety trocar instrument according to claim 13, further comprising a housing in which said trocar is mounted for said reciprocal movement, wherein said latch means comprises a pawl mounted with said housing, and wherein said trocar includes catch means engageable with said pawl when said trocar is moved to its projecting position.

15. The safety trocar instrument according to claim 14, wherein said trip means includes a trip member coupled to said pawl and coupleable to said trigger sleeve to disengage said pawl from said catch means, when said trigger sleeve returns to its extended rest position.

16. The safety trocar instrument according to claim 13, further comprising a housing, and wherein;

said latch means comprises a pawl mounted within said housing;
said trocar comprises catch means engageable with said pawl when said trocar is moved to its projecting position; and
said trip means comprises a trip member linked to said pawl and coupleable to said trigger sleeve when it is moved to its retracted position; and
said trigger sleeve moving said trip member when it returns to its extended rest position to disengage said pawl from said catch means permitting said trocar to move to its withdrawn rest position.

17. The safety trocar instrument according to claim 13, wherein said plunger means comprises means for gripping a portion of said trocar remote from said piercing point when said trocar is in the withdrawn rest position and for releasing said remote portion when said trocar reaches said projecting position.

18. The safety trocar instrument according to claim 17, wherein said plunger means further comprises a plunger head mounted for reciprocal movement relative to said trocar, and wherein said gripping means comprises at least one pusher element mounted in said plunger head, and means for driving said pusher element to grip said trocar in a radial direction and to release said trocar.

19. The safety trocar instrument according to claim 18, further comprising a housing with which said trocar and said plunger head are mounted for reciprocal movement in an axial direction;

wherein said plunger element has an outer cam surface and is mounted within said plunger for pivoted movement into and out of gripping engagement with said trocar; and
wherein said driving means comprises a cam driver mounted in said plunger head cooperating with said cam surface in a first position to hold said pusher element in gripping engagement with said trocar and in a second position to release said pusher element from gripping engagement with said trocar.

20. A safety trocar instrument for piercing a wall of an anatomical cavity, having an interior, to provide communication with the interior of the cavity, said trocar instrument comprising:
 (a) a main body-cannula subassembly including:
 (1) a main body;
 (2) a tubular cannula, having a distal end, projecting from the main body; and
 (b) a trigger sleeve-trocar subassembly formed to mate with said main body-cannula subassembly and including:
 (1) a housing;
 (2) a tubular trigger sleeve, having a distal end, mounted for axial reciprocal movement relative to said housing between a rest position extending from said housing and a retracted position retracted toward said housing; said trigger sleeve being formed to be coaxially received within said cannula when said trigger sleeve-trocar subassembly is mated with said main body-cannula subassembly;
 (3) means for urging said trigger sleeve toward its rest position;
 (4) an elongate trocar, having a sharp piercing point, mounted for axial reciprocal movement within said trigger sleeve between a withdrawn rest position in which said point is located within and shielded by the distal end of the trigger sleeve, and a projecting position in which said point protrudes beyond the distal end of said trigger sleeve;
 (5) means for biasing said trocar toward its withdrawn rest position;
 (6) plunger means with which said trigger-sleeve trocar subassembly can be manually urged toward said main body-cannula subassembly to an armed stage to cause the distal end of said trigger sleeve to project beyond the distal end of said cannula and to move said trocar to its projecting position in which said point also projects beyond the distal end of said trigger sleeve;
 (7) latch means for latching said trocar in the projecting position when the instrument is in an armed stage; and
 (8) trip means interconnecting said latch means and said trigger sleeve when said trigger sleeve moves to its retracted position in the armed stage, said trip means thereafter releasing latching of said trocar by said latch means when said trigger sleeve is urged to its rest position by said urging means thereby permitting said trocar to be urged to its rest position by said biasing means.

21. A safety trocar instrument for piercing a wall of an anatomical cavity, having an interior, to provide communication with the interior of the cavity, said trocar instrument comprising:
 (a) a tubular cannula having a distal end;
 (b) an elaborate trocar, having a sharp piercing point terminated in an extreme end, mountable for axial reciprocal movement within said cannula between a withdrawn rest position in which said point is received within and shielded by the distal end of said cannula and a projecting position in which said point is exposed beyond the distal end of said cannula;
 (c) means for biasing said trocar to its withdrawn position;
 (d) latch means for latching said trocar in the projecting position in opposition to said biasing means;
 (e) trip means for tripping said latching means to unlatch said trocar and thereby permitting said trocar to be moved to its withdrawn rest position by said biasing means;
 (f) mechanical trigger means mounted within said instrument, having a counterforce sensing portion locatable between the extreme end of said trocar point and the distal end of said cannula, said sensing portion sensing a counterforce exerted by the wall of the cavity after it has begun to be pierced by said trocar point and sensing relief of such counterforce when said sensing portion has pierced the wall of the cavity, said trigger means being mechanically coupleable to said trip means to cause said trip means to trip said latch means in response to sensing relief of such counterforce; said trigger means comprising a tubular trigger sleeve, having a distal end, in which said trocar is coaxially received, and said sensing portion comprising the distal end of said trigger sleeve, said trigger sleeve being receivable coaxially within said cannula and being mounted with said housing for axial reciprocal movement between an extended rest position with its distal end located between the extreme end of said trocar point and the distal end of said cannula and a retracted position with its distal end retracted toward the distal end of said cannula;
 (g) a housing; said latch means comprising a pawl mounted with said housing; said trocar comprising catch means engageable with said pawl when said trocar is moved to it projecting position; said trip means comprising a trip linked to said pawl and coupleable to said trigger sleeve when it is moved to its retracted position; wherein said trigger sleeve moves said trip member when it returns to its extended rest position to disengage said pawl from said catch means permitting said trocar to move to its withdrawn rest position; and
 (h) means for urging said trigger sleeve to the extended rest position.

* * * * *